United States Patent
West et al.

(10) Patent No.: US 8,901,329 B2
(45) Date of Patent: Dec. 2, 2014

(54) METHOD OF PRODUCING SATURATED ALKYL ESTERS/ACIDS

(75) Inventors: Ryan Michael West, West Chester, OH (US); Scott Leroy Cron, Liberty, OH (US); Jane Ellen Godlewski, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 190 days.

(21) Appl. No.: 13/616,397

(22) Filed: Sep. 14, 2012

(65) Prior Publication Data

US 2013/0066089 A1    Mar. 14, 2013

Related U.S. Application Data

(60) Provisional application No. 61/534,684, filed on Sep. 14, 2011.

(51) Int. Cl.
| | | |
|---|---|---|
| *C07C 51/00* | (2006.01) | |
| *C07C 59/147* | (2006.01) | |
| *C07C 59/185* | (2006.01) | |
| *C07C 67/327* | (2006.01) | |

(52) U.S. Cl.
CPC .................. *C07C 67/327* (2013.01)
USPC .......................... 554/148; 554/121

(58) Field of Classification Search
USPC .................................... 554/121, 148
See application file for complete search history.

(56) References Cited

FOREIGN PATENT DOCUMENTS

| WO | WO 2008/151178 A1 | 12/2008 | |
|---|---|---|---|
| WO | WO 2008151178 A1 * | 12/2008 | ............... C10G 3/00 |
| WO | WO 2010/144873 A1 | 12/2010 | |
| WO | WO 2010144873 A1 * | 12/2010 | |

OTHER PUBLICATIONS

International Search Report and Opinion for (PCT/US2012/055438) dated Nov. 15, 2012.

* cited by examiner

*Primary Examiner* — Deborah D Carr
(74) *Attorney, Agent, or Firm* — Brent M. Peebles

(57) ABSTRACT

Disclosed herein is the production of saturated alkyl esters or acids from furan materials. The starting compounds contain furan, ketone, and ester or acid functional groups and may be biologically-derived. The method includes hydrogenating the starting compound to form a reduced mixture. The method further includes hydrodeoxygenation of the reduced mixture to yield a saturated alkyl ester or acid. The saturated alkyl ester or acid can be unbranched or branched. The ester and acid products have a wide variety of applications and may be further processed into surfactants, solvents, and lubricants suitable for use in consumer products.

20 Claims, No Drawings

METHOD OF PRODUCING SATURATED ALKYL ESTERS/ACIDS

CROSS REFERENCE TO RELATED APPLICATION

This application claims the benefit of US Provisional Application No. 61/534,684 filed Sep. 14, 2011.

FIELD OF THE INVENTION

The invention relates to a method of producing saturated alkyl esters or acids. In particular, the invention relates to a method that includes hydrogenating and hydrodeoxygenating furan compounds containing an ester or acid functional group to make saturated unbranched and branched alkyl esters/acids. The ester or acid products of the invention may themselves be used in manufacturing or further processed into surfactants, solvents, and lubricants.

BACKGROUND OF THE INVENTION

Esters are essential components of many consumer and industrial products. Esters can be included in product formulations as raw materials and can also be converted into other additives, such as surfactants, solvents, and lubricants. For example, esters are routinely processed into alcohols and ultimately surfactants on an industrial scale for use in detergents. Given their widespread application, economical and environmentally-responsible methods of producing esters are desirable. Currently, the materials most commonly used to form esters are derived from oils or petroleum processes. A method of producing esters from renewable sources would therefore offer cost and energy savings over conventional processes. One readily available renewable source is biomass, which can include plant matter such as forestry and agricultural residues. The use of biomass in manufacturing is increasing in popularity, and biomass is routinely converted into furan compounds to produce fuels and industrial chemicals.

Current methods for processing furan compounds result in complete hydrogenation and deoxygenation of the starting materials. The end products from such processes are therefore predominantly alkanes. One example is the processing of furan compounds for use in jet fuel. The terms "furan compound" and "furan materials" as used herein, refer to compounds containing at least one furan ring. The furan compounds are hydrodeoxygenated using a bifunctional catalyst at a temperature of 275° C. to 295° C. and 6 MPa of pressure to produce liquid alkanes. Similar processes used to hydrodeoxygenate species with saturated furan and ketone functional groups using bifunctional catalysts and reaction conditions of 240° C. to 260° C. and 5 MPa to 6 MPa of pressure yield alkanes and only trace amounts of oxygen-containing species. The forgoing and other current hydrodeoxygenation process technologies do not allow for the production of compounds containing a single functional group, such as an ester. Maintaining ester functionality is advantageous because unlike alkanes, esters may be further processed into other additives such as surfactants, thereby increasing their range of use.

SUMMARY OF THE INVENTION

The present invention provides a method for producing saturated alkyl esters and acids. The method involves reacting an oxygenated hydrocarbon to form a saturated alkyl acid or ester where the oxygenated hydrocarbon contains at least one furan group, at least one oxygen-containing group selected from the group consisting of acid groups, ester groups, and combinations acid and ester groups, and at least one carbonyl-containing group selected from the group consisting of aldehyde groups, ketone groups, and combinations of aldehyde and ketone groups, wherein the method comprises first hydrogenating the oxygenated hydrocarbon in the presence of a first catalyst to reduce the number of multiple bonds and produce a reduced mixture having multiple components wherein each component of the reduced mixture contains at least one acid, ester or lactone group, and second hydrodeoxygenating the reduced mixture in the presence of a second catalyst to form a saturated alkyl acid or ester. The oxygenated hydrocarbon can additionally contain one or more alkene groups.

According to one embodiment, the method comprises catalytically hydrogenating a compound of Formula I:

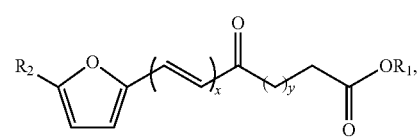

Formula I wherein $R_1$ is hydrogen or alkyl; $R_2$ is selected from the group consisting of hydrogen, alkyl, hydroxyalkyl and oxo-alkyl; x is 1 to 3; and y is 1 to 2. The ester or acid group is not reduced or eliminated during hydrogenation and the product of the reaction is a reduced mixture containing compounds with at least one fewer double bond along with an ester/acid moiety. The method further includes catalytically hydrodeoxygenating the resulting reduced mixture to open the oxygen-containing rings (e.g. furan, dihydrofuran, and tetrahydrofuran) and remove oxygen atoms. An ester or acid moiety is retained during hydrodeoxygenation to yield a saturated unbranched alkyl ester/acid product of Formula II:

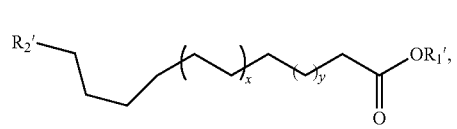

Formula II wherein $R_1'$ is hydrogen or alkyl, and $R_2'$ is the same as $R_2$, with the proviso that when $R_2$ is hydroxyalkyl or oxo-alkyl, $R_2'$ is the alkyl resulting from the hydrodeoxygenation of $R_2$.

According to another embodiment, the present invention may also be used to produce saturated branched alkyl esters or acids. The method includes catalytically hydrogenating a starting compound of Formula III:

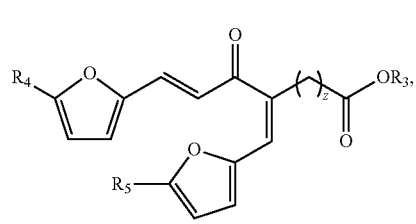

Formula III wherein $R_3$ is hydrogen or alkyl; $R_4$ and $R_5$ are each independently selected from the group consisting of hydrogen, alkyl, and hydroxyalkyl; and z is 1 to 2. The ester or acid group is not reduced or eliminated during hydrogenation, so the product of the reaction is a reduced mixture containing compounds with at least one fewer double bond along with an ester/acid moiety. The method further includes catalytically hydrodeoxygenating the resulting reduced mixture to open the oxygen-containing rings (e.g. furan, dihydrofuran, and tetrahydrofuran) and remove oxygen atoms. An ester or acid moiety is retained during hydrodeoxygenation to produce a saturated branched alkyl ester/acid product of Formula IV:

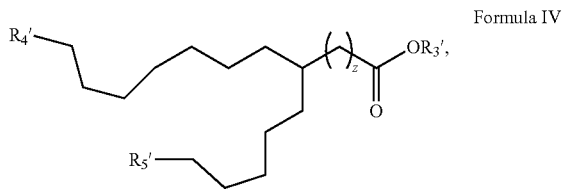

Formula IV wherein $R_3'$ is hydrogen or alkyl; $R_4'$ is the same as $R_4$, with the proviso that when $R_4$ is hydroxyalkyl, $R_4'$ is the alkyl resulting from the hydrodeoxygenation of $R_4$; and, $R_5'$ is the same as $R_5$, with the proviso that when $R_5$ is hydroxyalkyl, $R_5'$ is the alkyl group resulting from the hydrodeoxygenation of $R_5$.

According to a third embodiment, a saturated branched alkyl ester or acid may be made by first catalytically hydrogenating a compound of Formula V:

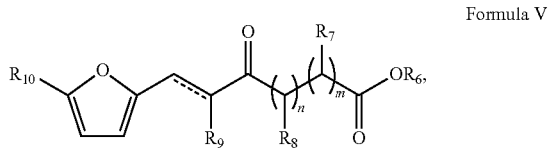

Formula V wherein the dashed line denotes an optional double bond; $R_6$, $R_7$, $R_8$, and $R_9$ are each independently hydrogen or alkyl; $R_{10}$ is selected from the group consisting of hydrogen, alkyl, and substituted alkyl; m is 1 to 4; and n is 1 to 4. The ester or acid group is not reduced or eliminated during hydrogenation, so the product of hydrogenation is a reduced mixture containing an ester/acid moiety. The method further includes hydrodeoxygenating the reduced mixture. An ester or acid moiety is retained during hydrodeoxygenation to yield a saturated branched alkyl ester/acid product of Formula VI:

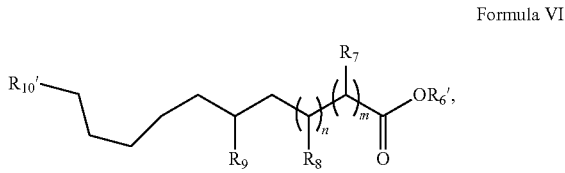

Formula VI wherein $R_6'$ is hydrogen or alkyl and $R_{10}'$ is the same as $R_{10}$ with the proviso that when $R_{10}$ is a substituted alkyl, $R_{10}'$ is the alkyl resulting from the hydrodeoxygenation of $R_{10}$.

The method of the present invention differs from current processes that completely deoxygenate furan compounds to produce alkanes. According to the present invention, an ester or acid functional group present in the starting compound is retained in the final product. The esters produced using the method of the present invention, and their corresponding acids and alcohols, may then be used in a variety of consumer and industrial products.

DETAILED DESCRIPTION OF THE INVENTION

It has been discovered that saturated alkyl esters and acids can be made from furan compounds. Suitable starting materials can be obtained from renewable biomass-derived species such as furfurals and acids. The present invention therefore provides a method of forming esters from carbohydrate-derived chemicals, instead of from oil- and petroleum-based materials. The starting materials can be obtained from a nearly limitless range of sources, including any lignin, hemicellulose, cellulose or methylcellulose-containing structures, such as trees and other plants. Utilizing carbohydrate-derived chemicals to form esters offers benefits in terms of cost and ease of production over methods currently in use. The method of producing esters from renewable sources also preserves resources and, therefore, is more environmentally-sound.

Disclosed herein are methods of making saturated branched or unbranched alkyl esters or acids. Generally, and as described in more detail below, the inventive method includes catalytically hydrogenating the starting compound, an oxygenated hydrocarbon to form a reduced mixture and then catalytically hydrodeoxygenating the reduced mixture to form the alkyl ester or acid. The starting materials for producing the esters and acids are compounds that include furan, ketone, and ester or acid functional groups. The starting materials may be formed by reacting an aldehyde containing compound with a ketone containing compound using methods described in U.S. Provisional Application Nos. 61/534,496, filed Sep. 14, 2011, and 61/669,775, filed Jul. 10, 2012, both entitled "Compounds and Methods for the Production of Long Chain Hydrocarbons From Biological Sources." by John Gordon, Louis Silks, Andrew Sutton, Ryan West, Dimitris Collias, and Ruilian Wu, the entire disclosures of which are incorporated herein by reference and referred to hereinafter as the "Gordon applications." The ester and acid products formed using the inventive method are suitable for a variety of applications and may be further processed to make alcohols, surfactants, solvents, lubricants, and fuels.

As used herein, "a saturated alkyl acid or ester" means a molecule containing at least one acid [—C=O(OH)] or ester [—C=O(OR), R=alkyl] functional group or groups connected to a hydrocarbon group wherein the hydrocarbon group can be linear, branched or cyclic, contains only carbon and hydrogen atoms, and each carbon in the hydrocarbon group is bound to four other atoms.

As used herein, "a reduced mixture" is a combination of individual molecules resulting from the hydrogenation of the initial oxygenated hydrocarbon wherein each resulting molecule has been reacted with at least one hydrogen molecule to produce a molecule with at least one fewer multiple bond than the initial oxygenated hydrocarbon. As used herein, "an oxygenated hydrocarbon" is a molecule containing only carbon, hydrogen and oxygen. Examples of individual functional groups and resulting functional groups when reacted with hydrogen to decrease the number of multiple bonds include, but are not limited to alkene to alkane, alkyne to alkene, ketone to secondary alcohol, aldehyde to primary alcohol, furan to dihydrofuran, furan to tetrahydrofuran, dihydrofuran to tetrahydrofuran, benzene to cyclohexane, benzene to cyclohexene, benzene to cyclohexa-diene, cyclohexa-diene to cyclohexene, cyclohexa-diene to cyclohexane, cyclohexene to cyclohexane, pyran to dihydropyran, pyran to tetrahydropyran, dihydropyran to tetrahydropyran, pyranone to dihydropyranone, pyranone to tetrahydropyranone, dihydropyranone to tetrahydropyranone, and furanone to dihydrofuranone.

In one embodiment, a method of reacting an oxygenated hydrocarbon to form a saturated alkyl acid or ester is provided. The oxygenated hydrocarbon contains at least one furan group, at least one oxygen-containing group selected from the group consisting of acid groups, ester groups, and combinations of acid and ester groups, and at least one carbonyl-containing group selected from the group consisting of aldehyde groups, ketone groups, and combinations of aldehyde and ketone groups. The method comprises hydrogenating the oxygenated hydrocarbon in the presence of a first catalyst to reduce the number of multiple bonds and produce a reduced mixture having multiple components wherein each component of the reduced mixture contains at least one acid, ester or lactone group; and hydrodeoxygenating the reduced mixture in the presence of a second catalyst to form a saturated alkyl acid or ester. In another embodiment, the oxygenated hydrocarbon further contains at least one alkene.

According to one embodiment, a saturated alkyl ester or acid may be made by catalytically hydrogenating a compound of Formula I:

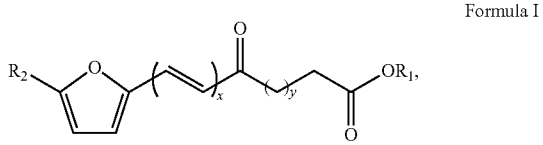

Formula I wherein x is 1 to 3; y is 1 to 3; $R_1$ is hydrogen or alkyl; and $R_2$ is selected from the group consisting of hydrogen, alkyl, hydroxyalkyl and oxo-alkyl, to form a reduced mixture. The term "oxo-alkyl" as used herein, refers to an alkyl chain containing a carbonyl having the general structure:

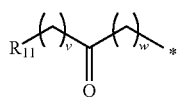

wherein the asterisk denotes the site of attachment to a furan ring.

In the compound of Formula I, $R_1$ may be hydrogen or an alkyl selected from the group consisting of methyl, ethyl, propyl, isopropyl, and butyl. Further, in the compound of Formula I, $R_2$ may be hydrogen; an alkyl selected from the group consisting of methyl, ethyl, propyl, and butyl; a hydroxyalkyl selected from the group consisting of hydroxymethyl, hydroxyethyl, hydroxypropyl, and hydroxybutyl; or an oxo-alkyl having the formula $R_{11}(CH_2)_vC(O)(CH_2)_w$—, wherein v is 0 to 3, w is 0 to 3, and $R_{11}$ is H or $CH_3$. Examples of suitable starting materials for making unbranched alkyl esters include, but are not limited to, compounds in which $R_1$ is hydrogen, methyl, or ethyl, and $R_2$ is hydrogen, methyl, hydroxymethyl, $CH_3C(O)(CH_2)_2$— or $CH_3C(O)$—.

Following hydrogenation, the reduced mixture is hydrodeoxygenated to remove oxygen atoms and form a saturated unbranched alkyl ester of Formula II:

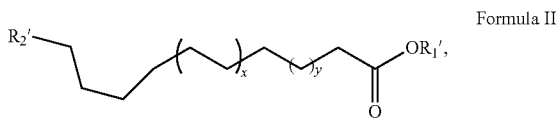

Formula II wherein $R_1'$ is hydrogen or alkyl, and $R_2'$ is the same as $R_2$ with the proviso that when $R_2$ is hydroxyalkyl or oxo-alkyl, $R_2'$ is the alkyl group resulting from the hydrodeoxygenation of $R_2$. The final product contains an acid or ester moiety. In certain embodiments, $R_1'$ is the same as $R_1$. In certain other embodiments, $R_1'$ is different from $R_1$. For example, in one embodiment, $R_1$ is hydrogen, and $R_1'$ is ethyl.

According to another embodiment, a saturated alkyl ester or acid may be made by catalytically hydrogenating a compound of Formula III:

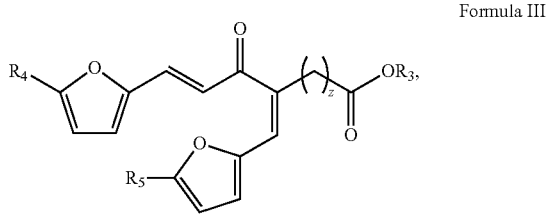

Formula III wherein z is 1 to 2; $R_3$ is hydrogen or alkyl; and $R_4$ and $R_5$ are each independently selected from the group consisting of hydrogen, alkyl, and hydroxyalkyl, to form a reduced mixture. In the compound of Formula III, $R_3$ may be hydrogen or an alkyl selected from the group consisting of methyl, ethyl, propyl, isopropyl, and butyl. Further, in the compound of Formula III, $R_4$ may be hydrogen; an alkyl selected from the group consisting of methyl, ethyl, propyl, and butyl; or a hydroxyalkyl selected from the group consisting of hydroxymethyl, hydroxyethyl, hydroxypropyl, and hydroxybutyl. Still further, in the compound of Formula III, $R_5$ may be hydrogen; an alkyl selected from the group consisting of methyl, ethyl, propyl, and butyl; or a hydroxyalkyl selected from the group consisting of hydroxymethyl, hydroxyethyl, hydroxypropyl, and hydroxybutyl. Examples of suitable starting materials for making branched esters include, but are not limited to, compounds in which $R_3$ is hydrogen, methyl or ethyl, $R_4$ is hydrogen, methyl, or hydroxymethyl, and $R_5$ is hydrogen, methyl, or hydroxymethyl.

Following hydrogenation, the reduced mixture is catalytically hydrodeoxygenated to remove oxygen atoms and form a saturated branched alkyl ester or acid of Formula IV:

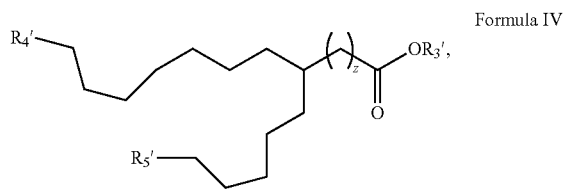

Formula IV wherein $R_3'$ is hydrogen or alkyl; $R_4'$ is the same as $R_4$, with the proviso that when $R_4$ is hydroxyalkyl, $R_4'$ is the alkyl resulting from the hydrodeoxygenation of $R_4$; and $R_5'$ is the same as $R_5$, with the proviso that when $R_5$ is hydroxyalkyl, $R_5'$ is the alkyl resulting from the hydrodeoxygenation of $R_5$. The final product contains an acid or ester moiety. In certain embodiments, $R_3'$ is the same as $R_3$. In certain other embodiments, $R_3'$ is different from $R_3$.

According to a third embodiment, a saturated alkyl ester or acid may be made by catalytically hydrogenating a compound of Formula V:

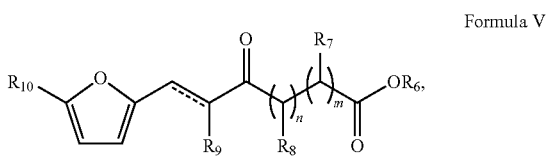

Formula V wherein the dashed line denotes an optional double bond; m is 1 to 4; n is 1 to 4; $R_6$, $R_7$, $R_8$, and $R_9$ are each independently hydrogen or alkyl; and $R_{10}$ is selected from the group consisting of hydrogen, alkyl, and substituted alkyl, to form a reduced mixture. The term "substituted alkyl" as used herein, refers to an alkyl radical wherein at least one hydrogen atom has been replaced with a functional group and includes oxoalkyl. Preferred functional groups include hydroxyl, halogen (F, Cl, Br), oxo, and alkoxy (alkyl-O—).

In the compound of Formula V, $R_6$ may be hydrogen or an alkyl selected from the group consisting of methyl, ethyl, propyl, isopropyl, butyl, pentyl and hexyl. Further, in the compound of Formula V, $R_7$, $R_8$, and $R_9$ may independently be hydrogen or an alkyl selected from the group consisting of methyl, ethyl, propyl, butyl, pentyl, and hexyl. Still further, in the compound of Formula V, $R_{10}$ may be hydrogen; an alkyl selected from the group consisting of methyl, ethyl, propyl, butyl, pentyl, and hexyl; or a substituted alkyl selected from the group consisting of substituted methyl, ethyl, propyl, butyl, pentyl, and hexyl. Examples of suitable starting materials include, but are not limited to, compounds in which $R_6$ is methyl or ethyl; $R_7$, $R_8$, and $R_9$ are independently hydrogen or methyl; and $R_{10}$ is hydroxymethyl, hydroxyethyl or oxoalkyl.

Following hydrogenation, the reduced mixture is catalytically hydrodeoxygenated to remove oxygen atoms and form a saturated branched alkyl ester of Formula VI:

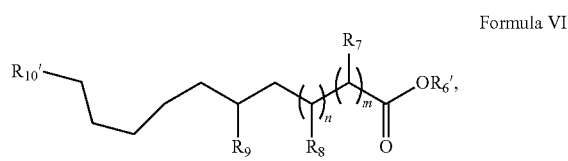

Formula VI wherein $R_6'$ is hydrogen or alkyl, and $R_{10}'$ is the same as $R_{10}$, with the proviso that if $R_{10}$ is a substituted alkyl, $R_{10}'$ is the alkyl resulting from the hydrodeoxygenation of $R_{10}$. The final product contains an acid or ester moiety. In certain embodiments, $R_6'$ is the same as $R_6$. In certain other embodiments, $R_6'$ is different from $R_6$. For example, in one embodiment, $R_6$ is ethyl and $R_6'$ is hydrogen or methyl.

The starting compound of Formula I, III or V may be obtained, for example, from reacting an aldehyde containing material with a ketone containing compound. The aldehyde containing material may be 2-furfural, hydroxymethyl furfural, or methyl furfural. The ketone containing material may be a levulinic ester or a species such as butanone, acetone, dihydroxyacetone, hydroxyacetone, 5-oxo-hexanoic acid, mixed pentanones or mixed hexanones. The aldehyde and ketone containing materials are commercially available and can also be made by a variety of methods, including the acid degradation and fermentation of sugars.

An example of a suitable reaction for forming the starting compound of Formula I, III, or V is an aldol condensation. Aldol condensation is a useful chemistry that involves the reaction of two carbonyl (C=O) compounds to form one compound joined by a carbon-carbon single bond, with the requirement that one of the carbonyls must possess a hydrogen atom in the alpha position relative to the carbonyl. When a second hydrogen is also in the alpha position relative to the carbonyl, the reaction is usually followed by the loss of water to form a conjugated species. An aldol condensation reaction may be catalyzed by a variety of catalysts, including bases. Strong bases such as sodium hydroxide and potassium hydroxide, as well as weaker bases such as sodium carbonate, have been shown to perform the reaction in water and organic solvents or under neat conditions, i.e. without solvent.

In one example of an aldol condensation between an aldehyde containing material and a ketone containing material, a furfural compound can be reacted with a neutralized acid such as levulinic acid (4-oxo pentanoic acid) or 5-oxo-hexanoic acid in water at a temperature of 50° C. to 100° C. to produce a species with more total carbons than the starting materials. After the reaction, the reaction mixture must be cooled, and acid must be added to convert the neutralized acid back into the acid form. Acid catalyzed esterification can then be performed in excess alcohol such as ethanol to form the ester. Single condensations between one aldehyde and one ketone may be used to form a compound of Formula I or V. Double condensations, wherein the product of a single condensation between one aldehyde and one ketone is further reacted with a second aldehyde, may be used to form a compound of Formula III. The total number of carbons in the resulting product depends on the number of carbons in the starting materials, as well as on the ratio of aldehydes to ketones and the reaction conditions. For example, a higher ketone-to-aldehyde molar ratio or a lower molar ratio of base present in the aqueous layer favors a single condensation product of Formula I over a double condensation product of Formula III, as described in West et al., "Liquid Alkanes with Targeted Molecular Weights from Biomass-derived Carbohydrates," ChemSusChem, 1:417-424 (2008), incorporated herein by reference.

In a starting compound of Formula I, $R_2$ may be an oxoalkyl group, preferably $CH_3C(O)(CH_2)_2$— or $CH_3C(O)$—. The oxo-alkyl group may be added to the furan ring in a chain elongation reaction using methods known in the art. For example, a compound of Formula I wherein $R_2$ is hydrogen can be reacted with an anhydride in the presence of a Lewis acid catalyst such as Ytterbium trifluoromethanesulfonate and solvent such as acetonitrile to convert $R_2$ to an oxo-alkyl. In another example, a compound of Formula I wherein $R_2$ is hydrogen can be reacted with methyl vinyl ketone in the presence of a Lewis acid or protic acid catalyst such as p-tolulenesulfonic acid and solvent such as acetonitrile to convert $R_2$ to an oxo-alkyl. Methods of producing the compound of Formula I wherein $R_2$ is an oxo-alkyl group and methods of producing the compound of Formula V are further described in the Gordon applications, the entire disclosure of which are incorporated herein by reference.

The scope of the current invention is not limited to oxygenated hydrocarbons that only contain furan, acid/ester, aldehyde/ketone, and alkene/alkane groups. Other functional groups can also be present including but not limited to aromatic, cyclic, alkyne, enol, pyran, lactone and ether groups.

In the case of lactone groups, a lactone will react to form an ester/acid group in the final alkyl ester. Lactone groups are cyclic esters wherein the singly-bonded oxygen connects back to the same carbon chain that links to the carbonyl carbon of the ester. Lactones can be an intermediate in the process, and can subsequently ring open to form an ester or acid. In the hydrodeoxygenation reaction a lactone will ring open to form an acid when water is present, an ester when an alcohol such as methanol is present, and a mixture of acid and ester when a mixture of water and alcohols are present.

Other functional groups such as aromatic, cyclic, alkyne, enol, pyran and ether groups, will react in such a way that no carbon to carbon bonds are broken. The only bonds to react are either multiple bonds or carbon to oxygen bonds with the exception of carbon to oxygen bonds that reside in the acid and ester groups; i.e. ester and acid groups remain intact. Ether groups, including cyclic ethers such as furans and pyrans, can react to remove the oxygen and replace it with hydrogen. In the case of a cyclic ether, after hydrodeoxygenation, the oxygen is removed and the cyclic structure ceases to exist. In the case of non cyclic ethers, two molecules are formed wherein each molecule has a hydrogen in place of the former attachment to oxygen. Carbocyclic structures that do not have an oxygen atom in the cyclic structure, however, will remain cyclic as no carbon to carbon bonds are broken. A substituted benzene or substituted phenol group will react to form a substituted cyclohexane group lacking any oxygen-containing substituents except for acid or ester groups.

Examples of how additional groups are expected to react are provided below to demonstrate the breadth of this invention wherein R and $R_2$ are H or alkyl.

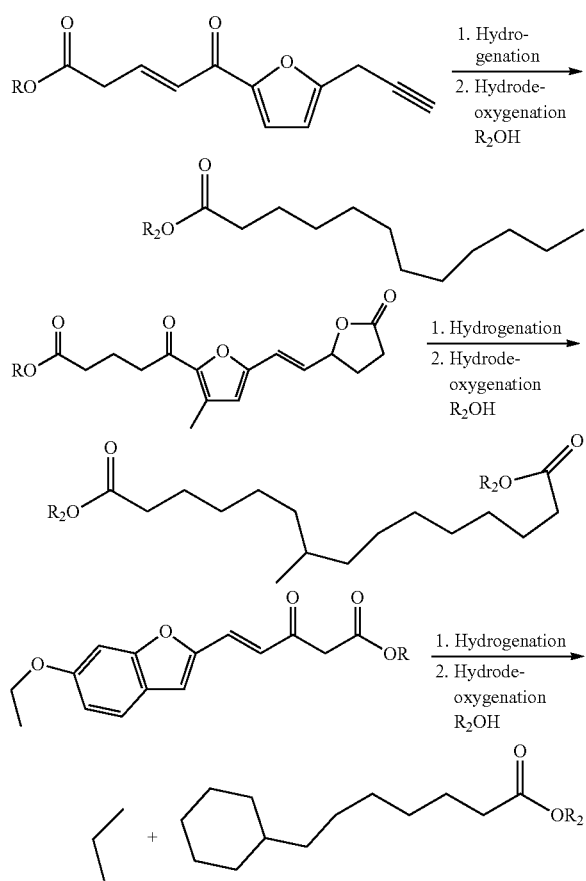

The present invention includes catalytically hydrogenating a compound of Formula I, III, or V. As used herein, the term "hydrogenation" (and variations thereof) refers to the addition of hydrogen to reduce multiple bonds within the starting compound. The hydrogenation step is important for preventing polymerization resulting in the formation of solids. Hydrogenation of the starting compound can also prevent large drops in pressure during subsequent reactions, such as hydrodeoxygenation. During hydrogenation, acyclic carbon-carbon double bonds are hydrogenated first, followed by hydrogenation of carbon-carbon double bonds in the furan ring(s) and lastly, hydrogenation of any ketone or aldehyde groups to form alcohols. Current methods for processing furan compounds remove all of the oxygen atoms from the starting compounds to produce alkanes, as described in U.S. Pat. No. 7,880,049, incorporated herein by reference. In contrast and according to the methods disclosed herein, the ester or acid functional group present in the starting compound is not reduced or eliminated during hydrogenation and is instead maintained in the end product.

The hydrogenation step of the present invention is performed in the presence of a first catalyst. Examples of suitable catalysts for hydrogenation include, but are not limited to: nickel, rhenium, ruthenium, palladium, platinum, rhodium, iridium, copper, chromium, iron, cobalt, and combinations thereof both individually and on a support. Hydrogenation can be performed under a variety of conditions, as a single reaction or in a series of separate reactions. One method of hydrogenation includes pressurizing a reactor containing the starting compound in a solvent such as ethanol or isopropyl alcohol, and catalyst, with hydrogen gas and stirring the reaction mixture until hydrogen uptake stops. Preferred conditions for the stirred reaction are about 50 psig to about 200 psig of hydrogen and about 50° C. to about 75° C. Hydrogenation can also be performed in a flow reactor, wherein the starting compound is first dissolved in a solvent such as ethanol and then flowed through a catalyst-loaded tube reactor under pressurized hydrogen. The preferred conditions for the flow reaction are about 35° C. to about 75° C. and about 400 psig of hydrogen. After hydrogenation is complete, the reaction mixture may be cooled to ambient temperature, filtered, and washed. The filtrate may then be evaporated to yield an oil product. The hydrogenation step reduces the starting material to a reduced mixture containing an ester or acid group. The reduced mixture is then hydrodeoxygenated to yield the saturated alkyl ester or acid product.

As used herein, the term "hydrodeoxygenation" (and variations thereof) refers to the reaction of hydrogen with a compound to remove oxygen atoms and multiple bonds in a compound. Hydrodeoxygenation opens the tetrahydrofuran ring(s) and removes oxygen atoms from alcohol and carbonyl groups. During hydrodeoxygenation, double bonds, either initially present or formed, are hydrogenated to form single bonds. In the present invention, the ester or acid group in the starting compound is not reduced or eliminated during hydrodeoxygenation. Hydrodeoxygenation may be performed as a single reaction step in the presence of a second catalyst, preferably in a flow reactor. Examples of suitable catalysts for hydrodeoxygenation include, but are not limited to, bifunctional catalysts composed of a metal on an acid support, such as platinum on a silica-alumina support or nickel on a silica-alumina or silica support. One method of catalyst preparation is incipient wetness impregnation of the acid support with a precursor salt, such as tetraamine platinum(II) nitrate. An aqueous solution of the salt is added dropwise to the support under constant stirring. The catalyst is then dried and calcined under dry air. Prior to hydrodeoxygenation, the catalyst is loaded into the flow reactor and reduced in situ by heating the reactor from room temperature, at about 25° C., to 450° C. over 8 hours under hydrogen gas flowing at atmospheric pressure at a Gas Hourly Space Velocity (GHSV, gas flow in units of volume per time divided by volume of catalyst) of between 100-500 $hr^{-1}$. Hydrodeoxygenation can also be performed as separate deoxygenation and hydrogenation steps. For the separate reactions, the deoxygenation step can be performed with an acid catalyst, and the hydrogenation can be performed with a metal catalyst.

Hydrodeoxygenation according to the method of the present invention may be performed by introducing the reduced mixture into a catalyst-loaded flow reactor with a hydrogen gas flow of 100-500 $hr^{-1}$. Preferably, the hydrodeoxygenation is performed at a temperature of about 220° C. to about 270° C. and about 3 MPa of hydrogen pressure. At temperatures higher than 270° C. for hydrodeoxygenation, metal catalysts can fully reduce the ester intermediates to alkane products. The method of the present invention limits alkane formation, resulting in a higher yield of the desired ester or acid. The reaction may be performed at a Liquid Hourly Space Velocity (LHSV, liquid flow in units of volume per time divided by volume of catalyst) of 0.3 to 1.7 hr$^{-1}$ over the course of several days. The liquid effluent obtained from the reaction system contains a spontaneously separating organic phase containing the saturated alkyl ester or acid end product.

During hydrodeoxygenation, the reduced mixture may be reacted neat, dissolved in an aqueous solution, or dissolved in an alcohol solvent such as methanol. For the neat reaction, the reduced mixture is introduced into the flow reactor in oil form. Alternatively, the reduced mixture may be dissolved in an aqueous solution and then flowed into the system. The aqueous solution may be composed of water and ethanol, preferably in a concentration of 60% water and 40% ethanol, based on the total weight of the solution. Dissolving the reduced mixture in a water-based feed facilitates the spontaneous separation of the product from the aqueous solution. The aqueous feed may also improve the reaction kinetics because the progressive removal of oxygen from the starting compound and intermediates towards the ester product creates an increasingly water-insoluble molecule. The hydrophobic ester may cease reacting as it is repelled from the surface of the polar catalyst. The reduced mixture may also be dissolved in methanol prior to being introduced into the flow reactor. The concentration of reduced mixture in methanol is preferably around 50 weight percent. The methanol-based feed may slow deactivation of the metal catalyst by reducing carboxylic acid formation and improve the yield of ester product, as the methyl ester.

Current methods of processing furan materials result in the production of alkanes and only trace amounts of oxygen-containing species. The method of the present invention encompassing hydrogenating and hydrodeoxygenating furan compounds allows for the retention of ester or acid functionality. The saturated unbranched or branched alkyl ester or acid products formed using the present invention may be used in a wide range of applications. The saturated unbranched ester or acid products of the present invention are direct renewable replacements for esters/acids currently used in manufacturing. The saturated branched ester or acid products are novel structures with the potential for widespread use as esters, alcohols and surfactants. The method of the present invention produces ester or acid products that, unlike the alkanes formed using other methods, may be further processed into other additives, such as surfactants, thereby increasing their overall utility.

The following Examples are provided to further illustrate the invention without being limiting. While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Examples 1 and 2 illustrate the method of producing a saturated unbranched alkyl ester. Examples 3 and 4 illustrate the method of producing a saturated branched ester. Example 5 illustrates the composition of products obtained using the present invention. Examples 6 to 8 illustrate the method of producing a saturated unbranched alkyl ester with different hydrodeoxygenation reaction conditions. Example 9 illustrates the effect of temperature and time on ester production. Example 10 illustrates and Examples 11 and 12 provide a method for making a saturated unbranched alkyl ester from a furan compound containing an oxo-alkyl functional group. Example 13 provides a method for making a saturated alkyl di-acid or di-ester.

EXAMPLE 1

Production of Ethyl Undecanoate from Ethyl 6-(5-methylfuran-2-yl)-4-Oxohex-5-Enoate To make a starting compound of Formula I, 11.5 mL of pyrrolidine (0.139 mol, 0.2 eq) and 8.0 mL of acetic acid (0.139 mol, 0.2 eq) were added to a solution of 100 g of ethyl levulinate (0.694 mol, 1.0 eq) in 400 mL of ethanol. To this solution, 76.4 g of 5-methyl-furfural (0.694 mol, 1.0 eq) was added over 30 minutes. The reaction was stirred at ambient temperature until complete, as analyzed by gas chromatography-mass spectrometry (GCMS). The reaction mixture was evaporated to dryness and dissolved in a mixture of 400 mL of hexane and 100 mL of ethyl acetate. Activated charcoal (Darco® G-60, Sigma-Aldrich) was added and stirred for 15 minutes. The reaction mixture was filtered over a six inch sintered glass funnel containing a six inch bed of silica and washed with 4:1 hexane/ethyl acetate to collect 7 fractions. Fractions 3 and 4 were combined and evaporated to an oil to give ethyl 6-(5-methylfuran-2-yl)-4-oxohex-5-enoate as an orange oil (114.6 g, 69.4% yield, proton nuclear magnetic resonance (HNMR), GCMS molecular weight=236).

For the hydrogenation reaction, 10 g of ethyl 6-(5-methylfuran-2-yl)-4-oxohex-5-enoate, 1 g of 10% wet weight basis Raney Nickel, 100 mL of ethanol, and 5 mL of water were combined in a Parr Bottle. The mixture was pressurized to 50 psi with hydrogen gas and heated to 70° C. The mixture was stirred until hydrogen uptake stopped. The mixture was cooled to ambient temperature, filtered, and washed with ethanol. The filtrate was rotary evaporated to yield ethyl 6-(5-methylfuran-2-yl)-4-oxohexanoate. The ethyl 6-(5-methylfuran-2-yl)-4-oxohexanoate (9.9 g) was then dissolved in hexanes solvent (Aldrich) and dried with sodium sulfate. The solids were filtered, and washed with hexanes. The hexane was combined with the liquid extract and evaporated to an oil. The oil was dissolved in 100 mL isopropyl alcohol (IPA) and added to a Parr bottle containing IPA-washed Raney Nickel (5.0 g wet weight). The reaction mixture was pressurized to 50 psi with hydrogen gas and heated to 70° C. The reaction mixture was stirred until hydrogen uptake stopped. The Raney Nickel was filtered off and washed with IPA. The IPA was then combined with the liquid extract and evaporated to produce ethyl 4-hydroxy-6-(5-methyltetrahydrofuran-2-yl) hexanoate.

To prepare the hydrodeoxygenation catalyst, incipient wetness was used to impregnate silica-alumina (SiAl; Siralox® 80/300) support with platinum (Pt). To 4 g of support, a solution of 5.20 g of water and 0.0801 g of tetraamine platinum (II) nitrate (Aldrich) was added dropwise under constant stirring. The resulting mixture was heated at 130° C. for about 12 hours in an oven. The dried sample was calcined under dry air flowing at a rate of about 50 mL/min by raising the temperature from room temperature, about 25° C. as used herein, to 450° C. at 175° C./hour and holding for 3 hours. After calcination, 1.5 g of 1% Pt on SiAl was loaded on a one-quarter inch stainless steel tube flow reactor and heated from room temperature to 450° C. over 8 hours under 25 mL/min (GHSV of ≈500 hr$^{-1}$) of flowing hydrogen gas at atmospheric pressure.

Ethyl 4-hydroxy-6-(5-methyltetrahydrofuran-2-yl)hexanoate (5 g) was dissolved in 45 g of water and 30 g of ethanol.

At a liquid flow rate of 0.02 mL/min (LHSV≈0.4 hr$^{-1}$), a temperature of 230° C., and pressure of 470 psig of hydrogen, a spontaneously separating organic phase containing ethyl undecanoate was collected. From 32 g of feed into the system, 1.34 g of organic phase was collected. GCMS analysis of the organic phase and comparison with NIST standards revealed the organic composition contained the following components (GCMS area %): decane (0.07%), undecane (0.53%), undecanol (0.78%), decane ethyl ester (0.67%), undecanoic acid/undecanoic ethyl ester (60.1%, mostly ethyl ester), and some unidentified peaks (37.85%).

The reaction scheme for Example 1 is as follows:

under 25 mL/min (GHSV of ≈500 hr$^{-1}$) of flowing hydrogen gas at atmospheric pressure. At a liquid flow rate of 0.02 mL/minute (LHSV≈0.4 hr$^{-1}$), temperature of 230° C., and pressure of 470 psig of hydrogen, a spontaneously separating organic phase containing ethyl undecanoate was collected. GCMS analysis of the organic phase revealed the organic composition contained the following components (GCMS area %): decane (0.6%), undecane (2.7%), undecanol (15.9%), decane ethyl ester (3.9%), undecanoic ethyl ester (27.6%), and some unidentified peaks (22.7%).

The reaction scheme for Example 2 is as follows:

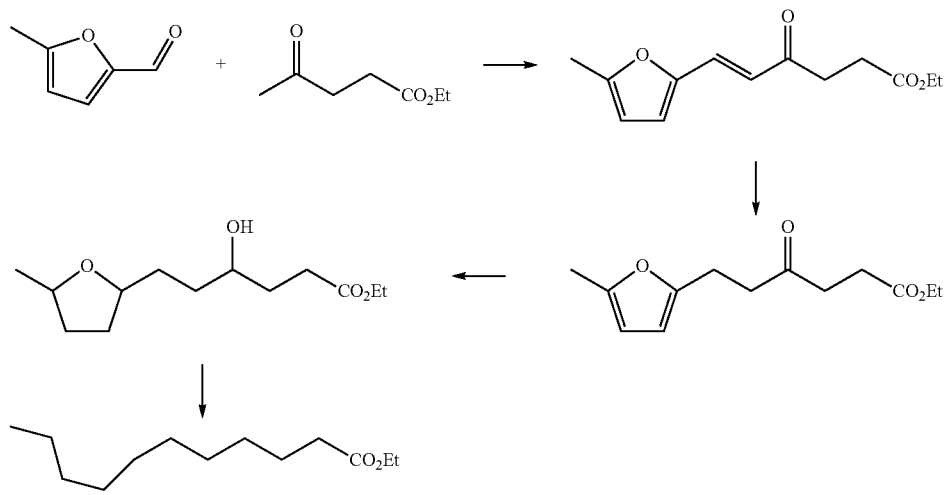

EXAMPLE 2

Production of Ethyl Undecanoate from Ethyl 6-(5-(hydroxymethyl)furan-2-yl)-4-Oxohex-5-Enoate For the hydrogenation reaction, 86 mL of isopropanol and 10 g of ethyl 6-(5-(hydroxymethyl)furan-2-yl)-4-oxohex-5-enoate were added to 1.6 g wet weight Raney Nickel. The

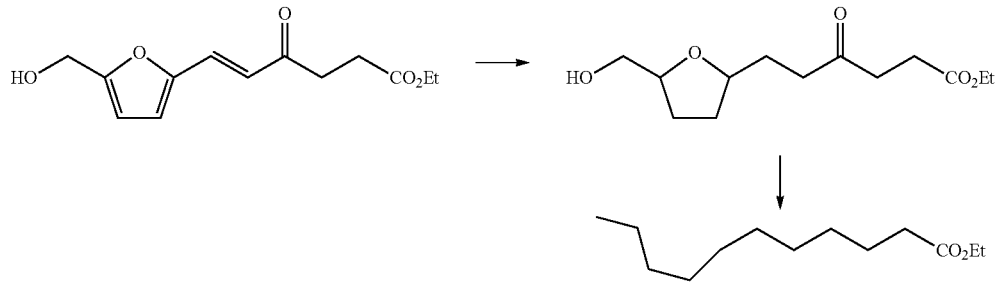

mixture was pressurized to 50 psi hydrogen and stirred at ambient temperature until hydrogen uptake stopped. The catalyst was filtered off and washed with IPA. The IPA was combined with the liquid filtrate and evaporated to produce ethyl 645-(hydroxymethyl)tetrahydrofuran-2-yl)-4-oxohexanoate, which was then dissolved in water at 10% concentration by weight.

For a hydrodeoxygenation catalyst, 1.5 g of 1% Pt on SiAl was loaded on a one-quarter inch stainless steel tube reactor and heated from room temperature to 450° C. over 8 hours

EXAMPLE 3

Production of Ethyl 3-Pentyldecanoate with Ru/C and Pt/SiAl catalysts

To prepare a starting compound of Formula III, 12 g of levulinic acid (0.104 mol, 1.0 eq) was first dissolved in 66 mL of water. A solution of 15.4 g of sodium carbonate (0.146 mol, 2.8 eq of base relative to levulinic acid) was slowly added. The resulting suspension was stirred for 30 minutes at room temperature. The reaction mixture was heated to 90° C., and a solution of 25 g of furfural (0.260 mol, 2.5 eq) in 25 mL of ethanol was added dropwise. The reaction mixture was stirred at 90° C. until complete, as determined by thin layer chromatography (TLC) (sys 9:1 CHCl$_3$/HOAc). The reaction mixture was cooled to room temperature, and the pH was carefully adjusted to pH=2 with concentrated HCl. The solids were removed by filtration and dissolved in ethyl acetate twice (400 ml). The ethyl acetate was treated with activated carbon, filtered and washed with ethyl acetate. Hexanes were added to the filtrate. The resulting slurry was filtered and washed with hexanes to give 6-(furan-2-yl)-3-(furan-2-ylmethylene)-4-oxohex-5-enoic acid as a brown solid (11.7 g, 41.3%, HNMR). A solution of 2 mL of sulfuric acid in 2 mL of ethanol was added to 10 g of 6-(furan-2-yl)-3-(furan-2-ylmethylene)-4-oxohex-5-enoic acid (0.0367 mol, 1.0 eq) in 100 mL of ethanol. The mixture was heated to reflux and stirred until complete, as determined by TLC (sys: 100% EtOAc). The reaction mixture was cooled to room temperature and poured slowly into a saturated sodium bicarbonate solution. The product was extracted with ethyl acetate, washed with saturated brine, treated with activated carbon and dried with sodium sulfate. The filtrate was evaporated to dryness to give ethyl 6-(furan-2-yl)-3-(furan-2-ylmethylene)-4-oxohex-5-enoate as an oil (9.7 g, 88% yield, HNMR, carbon nuclear magnetic resonance ($^{13}$CNMR)).

For the hydrogenation reaction, 7.75 g of 5 weight percent ruthenium (Ru) on carbon (C) catalyst (Alfa Aesar) was packed between quartz wool in a one-half inch stainless steel tube reactor and heated to 100° C. under 100 mL/min (GHSV of ≈350 hr$^{-1}$) of flowing hydrogen gas. Ethyl 6-(furan-2-yl)-3-(furan-2-ylmethylene)-4-oxohex-5-enoate was reduced in the catalyst bed by first dissolving the compound in ethanol to form a feed and then flowing the feed through the stainless steel tube at a temperature of 50° C. to 75° C. and 400 psig of hydrogen over 44.5 hours. A sample of feed was collected and rotary evaporated to a yellow oil (Oil 1). GCMS analysis revealed little to no unsaturated species of ethyl 6-(furan-2-yl)-3-(furan-2-ylmethylene)-4-oxohex-5-enoate, except for a small quantity of the saturated ketone, ethyl 4-oxo-6-(tetrahydrofuran-2-yl)-3-((tetrahydrofuran-2-yl)methyl)hexanoate, which was less than 10% by GCMS area.

The remaining feed was pumped through the one-half inch tube at a temperature of 35° C. and 400 psig over 44 hours. Ethanol was then pumped through the reactor at a rate of 14.8 g over 4 hours for 128.5 g total. A sample of feed was collected and rotary evaporated to give an orange-brown oil (Oil 2). GCMS analysis revealed mostly ethyl 4-oxo-6-(tetrahydrofuran-2-yl)-3-((tetrahydrofuran-2-yl)methyl)hexanoate, 80% to 90% by GCMS area.

For the hydrodeoxygenation reaction, 7.08 g of 1% Pt on SiAl was loaded in a one-half inch reactor, and heated from room temperature over 8 hours to 450° C. under 100 mL/min of flowing hydrogen gas (GHSV of ≈350 hr$^{-1}$) at atmospheric pressure. All reactions were run at 235° C. and 470 psig of hydrogen with a hydrogen gas flow of 30 mL/min to 60 mL/min (GHSV of ≈400-220 hr$^{-1}$).

Oil 1 (6.1 g) was dissolved in 31.48 g of water and 19 g of ethanol to form a feed. A total of 56.6 g of the feed was flowed into the system over 23 hours, and 52.55 g of liquid effluent (Effluent 1) was collected, including 2.71 g of spontaneously separating organic phase (Organic 1).

Oil 2 (9.66 g) was dissolved in 51.09 g of water and 36.88 g of ethanol to form a feed (Feed 2). A total of 40.73 g of Feed 2 was flowed into the system over 7.25 hours, and 33.46 g of liquid effluent (Effluent 2) was collected, including 1.36 g of spontaneously separating organic phase (Organic 2). The system was flushed with 13.7 g of water over about 48 hours to recover 18 g of effluent (Effluent 2A) containing 1.80 g of spontaneously separating organic phase (Organic 2A). The feed lines were reprimed with 5 g of Feed 2, and then 52 g of Feed 2 was flowed into the system for 19.25 hours, and 42.9 g of liquid effluent (Effluent 2B) was collected, including 3.75 g of spontaneously separating organic phase (Organic 2B).

The reaction scheme for Example 3 is as follows:

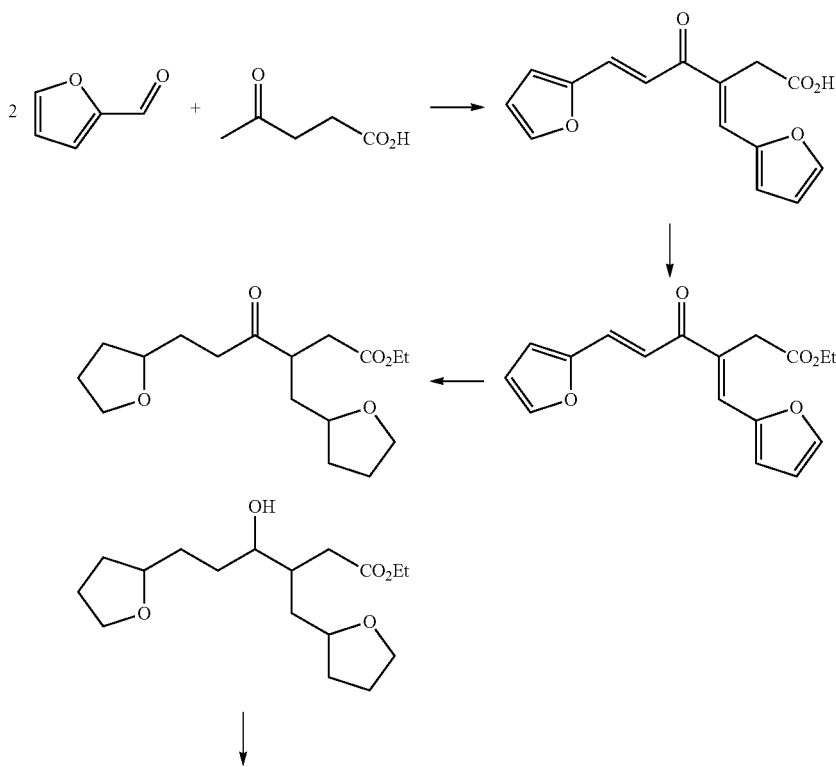

-continued

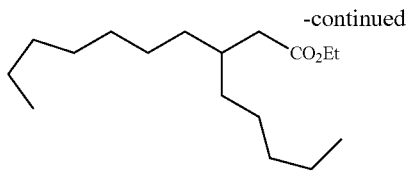

EXAMPLE 4

Production of Ethyl-3-Pentyldecanoate with Ni/SiO$_2$, Ru/C, and Pt/SiAl Catalysts A starting compound of Formula III was produced as described in Example 3. For the hydrogenation reaction, ethyl 6-(furan-2-yl)-3-(furan-2-ylmethylene)-4-oxohex-5-enoate (82 g wet solid) was reduced with 5.2 g of 64% nickel (Ni) on silicon dioxide (SiO$_2$) (BASF) in 320 g of ethanol in a 600 mL Parr reactor stirred at 700 rpm. The reactor was purged of air using vacuum and nitrogen cycles and then charged with hydrogen gas to an initial pressure of 150 psig. The mixture was heated to 50° C. with stirring at 700 rpm. Hydrogen was charged to a final pressure of 200 psig and maintained at this pressure for 64 hours. After 64 hours, the temperature of the reactor was increased to 75° C. and heated for 6 more hours. The effluent was collected after cooling the reactor and releasing the pressure and then pumped through the one-half inch stainless tube containing the Ru on C catalyst described in Example 3 at a temperature of 35° C. to 55° C. and 400 psig over 37.5 hours to remove the remaining furan groups. The effluent was collected and rotary evaporated to give a brown oil (Oil 3). GCMS analysis of the reduced mixture revealed mostly ethyl 4-oxo-6-(tetrahydrofuran-2-yl)-3-((tetrahydrofuran-2-yl)methyl)hexanoate, 85 to 95% by GCMS area.

For the hydrodeoxygenation reaction, 7.08 g of 1% Pt on SiAl was loaded on a one-half inch diameter reactor and heated from room temperature over 8 hours to 450° C. under 100 mL/min (GHSV of ≈350 hr$^{-1}$) of flowing hydrogen gas at atmospheric pressure. All reactions were run at 235° C. and 470 psig of hydrogen with a hydrogen gas flow of 30 to 60 mL/min (GHSV of ≈100-220 hr$^{-1}$). Oil 3 (55.40 g) was dissolved in 252.69 g of water and 191.91 g of ethanol to form a feed. A total of 489.8 g of the feed was flowed into the system over 153.5 hours, and 489.8 g of liquid effluent (Effluent 3) was collected, including 42.78 g of spontaneously separating organic phase (Organic 3). The system was flushed with 35 g of acetone for 68 hours to recover 30.7 g of effluent (Effluent 3A) containing 9.33 g of spontaneously separating organic phase (Organic 3A).

EXAMPLE 5

Fractional Distillation of Organic Phase

Effluents 1, 2, 2A, 2B, 3, and 3A and organic phases Organic 1, 2, 2B, 3, and 3A from Examples 3 and 4 were extracted twice with hexanes 1:1 on a volume basis. The hexanes were rotary evaporated to give 50.17 g of oil. The oil was combined with organic phase Organic 2A from Example 3 and distilled to give various fractions. Species were identified by hydrogen nuclear magnetic resonance (HNMR), carbon nuclear magnetic resonance (CNMR) and GCMS and classified into 5 categories. After distillation, 46.78 g of material out of a possible 51.82 g was recollected. All distillations were performed at 0.20 mm Hg. Alkanes included C13 to C15 branched saturated species that were collected at a pot temperature of 100° C. to 115° C. and a distillate temperature of 30° C. to 90° C. Intermediates, representing a mixture of species including C15 alkanes, C15 ethyl ester and species with boiling points between those species were collected at a pot temperature of 125° C. and a distillate temperature of 90° C. The C15 ethyl ester was collected at a pot temperature of 150° C. to 190° C. and a distillate temperature of 90° C. to 110° C. Higher Boilers, i.e. species that boil at a temperature above the ethyl ester, were collected at 219° C. to 246° C. and a distillate temperature of 93° C. to 125° C. The latter distillate temperature was cooler than previous points, but also associated with a very slow collection of material. The pot bottoms were categorized as Very High Boiler. From the 60.7 g of theoretical maximum and 50.17 g of oil, 25.1 g (41.4% of theoretical) of C15 ester (ethyl 3-pentyldecanoate), with a small amount of the corresponding acid, was collected. The distribution of species after fractional distillation was 53% Ethyl Esters, 19% Alkanes, 17% Very High Boiler, 10% Higher Boiler, and 1% Intermediates.

EXAMPLE 6

Production of Ethyl Dodecanoate Using a Neat Reaction

To prepare a starting compound of Formula I, 27 g of pyrrolidine (0.38 moles) followed by 34 g of acetic acid (0.57 moles) were added to an iced solution of 209 g of 5-methylfurfural (1.9 moles) and 300 g of ethyl 4-acetylbutyrate (1.9 moles). The resultant solution was allowed to warm to ambient temperature and stirred for 48 hours. The resultant solution was diluted with an equal volume diethyl ether and washed with, in succession: 300 mL brine, 300 mL 1N hydrochloric acid, 300 mL saturated sodium bicarbonate, and 300 mL brine. The resultant solution was then dried over anhydrous magnesium sulfate, filtered and stripped of solvent. The resultant oil (479 g) was purified by short path vacuum distillation. A light yellow oil (375 g) was collected at 158° C. to 160° C. and 0.2 mm Hg. The resultant product, ethyl 7-(5-Methylfuran-2-yl)-5-oxo-hept-6-enoic acid ethyl ester, was shown to be 99.3% pure by GC with structure confirmed by GCMS (79% yield).

For the hydrogenation reaction, 289 g of 7-(5-Methylfuran-2-yl)-5-oxo-hept-6-enoic acid ethyl ester, and 3.0 g of 64 weight percent Ni on Silica were added to a 600 mL stirred Parr reactor. The reactor was purged of air using vacuum and nitrogen cycles and then charged with hydrogen to an initial pressure of 200 psig with stirring at 700 rpm, used throughout. The system was run at 200 psig of hydrogen with temperatures of 75° C. for 4 hours, then 100° C. for 2 hours, and then 125° C. for 12 hours. The hydrogen pressure was then increased to 1100 psig, and the reactor was run at 150° C. for 29 hours, and then at 200° C. for 2 hours. GCMS analysis suggested the reduced mixture contained ethyl 7-(5-methyltetrahydrofuran-2-yl)-5-oxoheptanoate, as well as the corresponding alcohol, ethyl 5-hydroxy-7-(5-methyltetrahydrofuran-2-yl)heptanoate.

To prepare the hydrodeoxygenation catalyst, incipient wetness was used to impregnate silica-alumina (Siralox 80/300) with nickel. To 8.07 g of support, a solution of 10.28 g of water and 0.398 g of Ni(NO$_3$)$_2$.6H$_2$O (Aldrich) was added dropwise under constant stiffing. The resulting mixture was heated at 130° C. for about 12 hours in an oven. The dried sample was calcined under dry air flowing at a rate of 50 mL/min by ramping the temperature from room temperature to 300° C. at 175° C./hour and holding for 3 hours. In preparation for the hydrodeoxygenation reaction, 5.56 g of 1% Ni on SiAl was loaded into a one-half inch diameter stainless steel tube and heated from room temperature over 8 hours to 450° C. under 25 mL/min (GHSV of ≈200 hr$^{-1}$) of flowing hydrogen gas at atmospheric pressure.

Neat ethyl 7-(5-methyltetrahydrofuran-2-yl)-5-oxoheptanoate was flowed at a pressure of 470 psig, and temperature of 240° C. under flowing hydrogen gas for 28 hours. The liquid flow rate and hydrogen gas flow rates were kept constant relative to each other, e.g. 0.03 mL/min liquid flow and 30 mL/min gas flow; 0.06 and 60 mL/min; or 0.09 and 90 mL/min The effluent was primarily organic with a small spontaneously separating water layer beneath the organic phase. Not counting the startup and shutdown, 62.9 g of organic phase was collected out of a theoretical 68.5 g, or 91.9%. GCMS analysis revealed an initial high concentration of 58.2% ethyl dodecanoate, 28.7% dodecanoic acid, and 13% intermediates, possibly ethyl 7-(5-methyltetrahydrofuran-2-yl)heptanoate.

The reaction scheme for Example 6 is as follows:

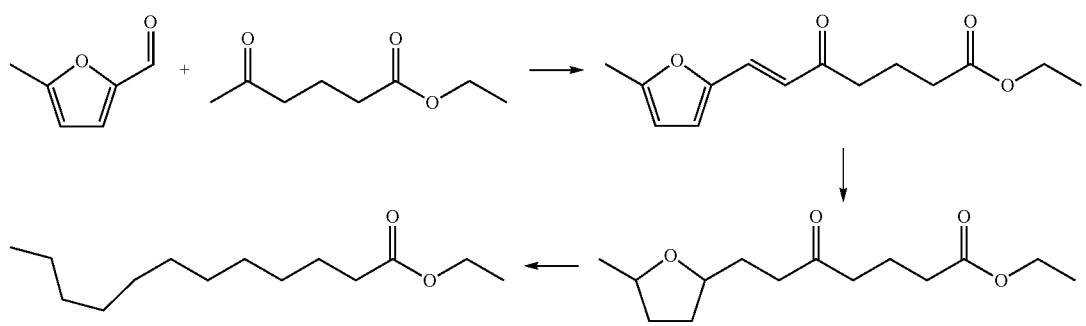

EXAMPLE 7

Production of Ethyl Dodecanoate Using a Water-Based Feed

The production of the starting compound, 7-(5-Methyl-furan-2-yl)-5-oxo-hept-6-enoic acid ethyl ester, and hydrogenation reaction were performed as described in Example 6. For the hydrodeoxygenation reaction, ethyl 7-(5-methyltetrahydrofuran-2-yl)-5-oxoheptanoate and ethyl 5-hydroxy-7-(5-methyltetrahydrofuran-2-yl)heptanoate were dissolved at 15 weight percent to 17 weight percent in a water and ethanol solution composed of about 60% water and about 40% ethanol. The solution was pumped at a rate of 0.08 mL/min (LHSV≈0.3 hr$^{-1}$) over the 7.08 g Pt on SiAl tubular bed described in Example 3 at a temperature of 240° C., pressure of 470 psig and hydrogen gas feed of 30 mL/min (GHSV≈100 hr$^{-1}$) for 6 continuous days. The effluent from the flow reactor spontaneously separated into two components: a less dense organic phase, and a more dense aqueous phase. The organic phase was collected and analyzed. A total of 78.5 g of organic phase was collected, including start up and shut down. GCMS analysis showed the major components to be 93% ethyl dodecanoate and 6% dodecanoic acid.

EXAMPLE 8

Production of Methyl Dodecanoate Using a Methanol-Based Feed

The starting compound, 7-(5-Methyl-furan-2-yl)-5-oxo-hept-6-enoic acid ethyl ester, was prepared as described in Example 6. For the hydrogenation reaction, 484.2 g of 7-(5-Methyl-furan-2-yl)-5-oxo-hept-6-enoic acid ethyl ester and 3.0 g of 64 weight percent Ni on Silica catalyst were added to a 600 mL stirred Parr reactor. The reactor was purged of air using vacuum and nitrogen cycles and then charged with hydrogen to an initial pressure of 200 psig with stirring at 700 rpm, used throughout. The system was run at 200 psig of hydrogen with temperatures of 75° C. for 4 hours, then 100° C. for 2 hours, and then 125° C. for 82 hours. Additional catalyst (13.6 g) was added, and the reaction was run at 125° C. for 24 hours. The hydrogen pressure was then increased to 1100 psig hydrogen, and the reactor was run at 150° C. for 25 hours. GCMS analysis suggested the reduced mixture contained both ethyl 5-hydroxy-7-(5-methyltetrahydrofuran-2-yl)heptanoate and the corresponding lactone 6-(2-(5-methyltetrahydrofuran-2-yl)ethyl)tetrahydro-2H-pyran-2-one.

The same procedure for hydrodeoxygenation catalyst preparation described in Example 6 was utilized to create a 10 weight percent Ni on SiAl catalyst using 3.98 g of Ni(NO$_3$)$_2$.6H$_2$O. To prepare the catalyst, 1.04 g of 10% Ni on SiAl was loaded into a one-quarter inch diameter stainless steel tube and heated from room temperature over 2 hours to 350° C. under 30 mL/min (GHSV≈600 hr$^{-1}$) of flowing hydrogen gas at atmospheric pressure. The mixed product from the previous step was dissolved at 50 weight percent in methanol. The solution was pumped at 0.03 mL/min (LHSV≈0.60 hr$^{-1}$) over the 10% Ni on SiAl at a temperature range of 220° C. to 270° C., pressure of 470 psig of hydrogen, and hydrogen gas feed of 100 mL/min (GHSV≈1000 hr$^{-1}$). The effluent from the flow reactor spontaneously separated into two components: a less dense organic phase, and a more dense aqueous phase. The organic phase was collected, measured, and analyzed by GC and GCMS. The use of methanol decreased the production of dodecanoic acid, as compared to the neat reaction and water-based feed.

EXAMPLE 9

Effect of Temperature and Time on Ester Production

The hydrodeoxygenation of the mixed product described in Example 8 was run at temperatures between 222° C. and 267° C. for up to 170 hours. Multiple data points were taken, analyzed on flame ionization detector (FID) GC, and averaged for the temperature and time conditions described in Table 1. At a temperature of 250° C. and 5 hours on stream, 79% alkane products (undecane and dodecane) was observed, while only 6.5% desired esters (methyl dodecanoate and ethyl dodecanoate) was observed. At a temperature of 222° C. and 25 hours, 1.1% alkanes was observed, and 37.1% esters was observed. Additionally, 32% of the suspected intermediate species was seen. At 49 hours and a temperature of 235° C., 4.1% alkanes was observed, and 62.6% desired esters was observed. Additionally, some suspected intermediate species such as lactones (delta-dodecalactone) and esters containing a saturated furan ring were observed at 1%. At 77 hours on stream and a temperature of 251° C., 11.8% alkanes was observed, and 68.4% desired esters was observed. Suspected intermediate species were observed at 0.4%. At a temperature of 267° C. at 98 hours, 11.9% alkanes and 70.2% desired esters were observed with 0.4% suspected intermediates. At temperatures from 253 to 255° C. and time on stream from 112 to 170 hours, the total observed alkane dropped from 6.4% to 1.3% to 1.8%, while the total desired ester increased from 77.8% to 86.1%. The suspected intermediates also increased from 0.4% to 2.4%. Table 1 describes the compositions of the organic phases obtained after hydrodeoxygenation at the different temperatures and times.

resulting reduced mixture suggested the following components: ethyl 4-oxo-6-(5-(3-oxobutyl)tetrahydrofuran-2-yl)hexanoate, ethyl 4-hydroxy-6-(5-(3-hydroxybutyl)tetrahydro-furan-2-yl)hexanoate, and 5-(2-(5-(3-hydroxybutyl)tetrahydrofuran-2-yl)ethyl)dihydrofuran-2(3H)-one.

A total of 6.65 g of the catalyst described in Example 8, 10% Ni on SiAl, was loaded into a one-half inch stainless steel tube and heated from room temperature over 2 hours to 350° C. under 30 mL/min (GHSV≈100 hr$^{-1}$) of flowing hydrogen gas at atmospheric pressure. The mixed product from the previous step was dissolved at 50 weight percent in methanol. The solution was pumped at 0.20 mL/min (LHSV≈0.70 hr$^{-1}$) over the 10% Ni on SiAl catalyst at a temperature of 242° C. to 246° C., pressure of 470 psig of hydrogen, and hydrogen gas feed of 200 mL/min (GHSV≈700 hr$^{-1}$). The effluent from the flow reactor spontaneously separated into two components: a less dense organic phase and a more dense aqueous phase. The organic phase was collected, measured, and analyzed by GC and GCMS.

At temperatures from 242° C. to 246° C. and time on stream from 3 to 11 hours, the total observed alkane (tetradecane) dropped from 4.7% to 2.8%, while the total desired esters (methyl and ethyl tetradecanoate) increased from 76.5% to 91.1%. Table 2 describes the compositions of the

TABLE 1

| | Time on Stream (hours) | | | | | | | |
|---|---|---|---|---|---|---|---|---|
| | 5 | 25 | 49 | 77 | 98 | 112 | 139 | 170 |
| | Temperature (° C.) | | | | | | | |
| | 250 | 222 | 235 | 251 | 267 | 253 | 255 | 253 |
| Undecane | 24.7% | 0.3% | 1.5% | 4.0% | 4.5% | 2.2% | 0.7% | 0.9% |
| Dodecane | 54.3% | 0.7% | 2.7% | 7.8% | 7.4% | 4.2% | 0.6% | 0.9% |
| 2-Methyl 5-Hexyl THF | 0.0% | 9.7% | 7.4% | 0.9% | 0.3% | 0.8% | 0.6% | 1.2% |
| Dodecanols | 7.2% | 3.7% | 7.6% | 6.9% | 4.6% | 4.4% | 2.5% | 2.8% |
| Methyl Dodecanoate | 4.6% | 32.8% | 57.3% | 62.0% | 63.7% | 71.2% | 75.5% | 79.4% |
| Dodecanoic Acid | 0.0% | 0.6% | 1.9% | 3.9% | 6.4% | 3.5% | 6.0% | 2.3% |
| Ethyl Dodecanoate | 2.0% | 4.3% | 5.3% | 6.4% | 6.5% | 6.6% | 8.4% | 6.7% |
| Suspected Intermediates | 3.7% | 32.0% | 1.0% | 0.4% | 0.4% | 0.4% | 0.3% | 2.4% |
| Fatty Esters | 0.0% | 4.6% | 8.9% | 1.2% | 0.9% | 0.7% | 3.8% | 0.7% |
| Other | 3.6% | 11.3% | 6.6% | 6.6% | 5.3% | 6.0% | 2.6% | 3.4% |

EXAMPLE 10

Production of Methyl Tetradecanoate and Ethyl Tetradecanoate from Ethyl 4-oxo-6-(5-(3-oxobutyl)furan-2-yl)hexanoate Furfural, ethyl levulinate and methyl vinyl ketone were reacted to form the starting compound, ethyl 4-oxo-6-(5-(3-oxobutyl)furan-2-yl)hexanoate, according to a method described in the Gordon applications, the entire disclosure of which are incorporated herein by reference.

For the hydrogenation reaction, 95.5 g of ethyl 4-oxo-6-(5-(3-oxobutyl)furan-2-yl)hexanoate, 100 g of ethanol and 20.8 g of 64 weight percent Ni on Silica were added to a 600 mL Parr reactor. Alternative catalysts such as Rh, Re, Ru, Pd, Pt, Ir, Cu, Cr, or Fe on supports such as carbon, silica, or alumina can also be used. The reactor was purged of air using vacuum and nitrogen cycles and then charged with hydrogen to an initial pressure of 200 psig with stirring at 700 rpm, used throughout. The system was run at 200 psig of hydrogen with a temperature of 75° C. for 37 hours. GCMS analysis of the organic phases obtained after hydrodeoxygenation at the different times as analyzed by FID GC.

TABLE 2

| | Time on stream (hours) | | | |
|---|---|---|---|---|
| | 3.2 | 5.2 | 6.9 | 11.2 |
| | Temperature ° C. | | | |
| | 242 | 246 | 243 | 242 |
| Tetradecane | 4.7% | 2.0% | 1.8% | 2.8% |
| n-tetradecanol | 3.2% | 1.9% | 1.8% | 1.2% |
| Methyl Tetradecanoate | 70.2% | 76.6% | 77.7% | 83.3% |
| Tetradecanoic Acid | 0.0% | 0.8% | 1.8% | 0.0% |
| Ethyl Tetradecanoate | 6.3% | 7.3% | 7.7% | 7.8% |
| Fatty Esters | 7.2% | 7.9% | 8.1% | 4.9% |
| Other | 8.4% | 3.5% | 1.1% | 0.0% |

The reaction scheme for Example 10 is as follows:

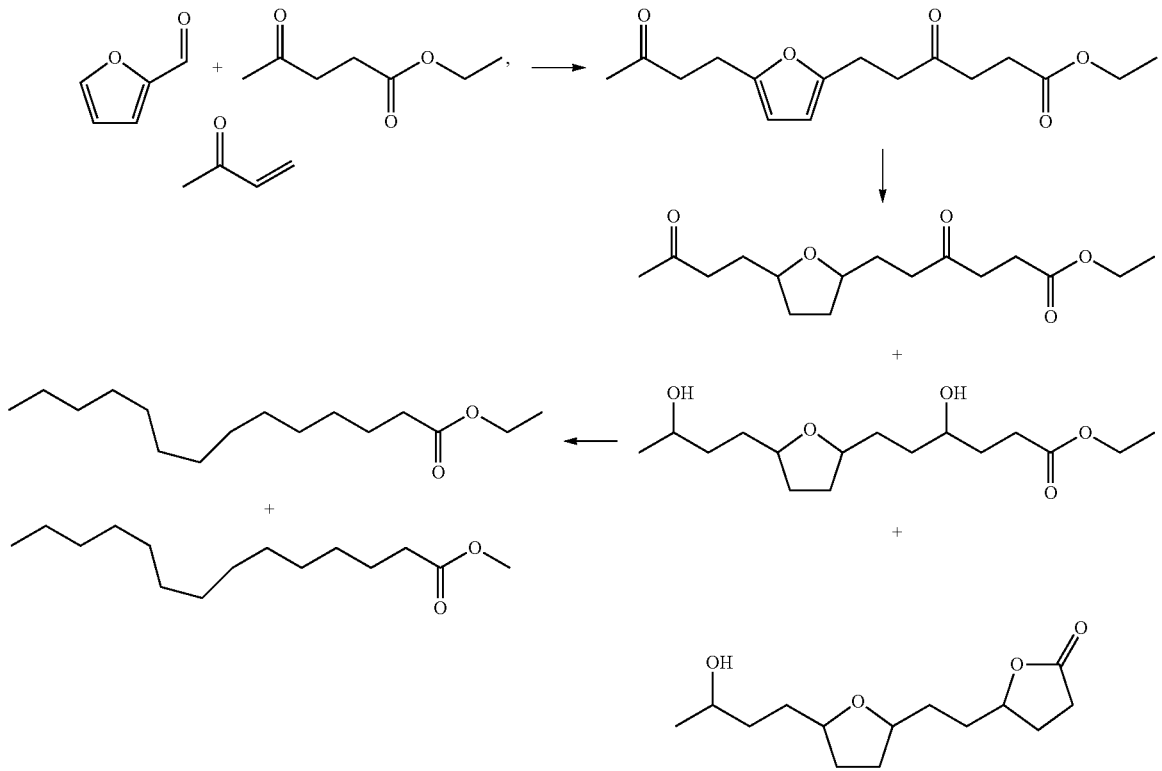

EXAMPLE 11

Method for Producing Methyl Dodecanoate and Ethyl Dodecanoate from Ethyl 6-(5-acetylfuran-2-yl)-4-oxohexanoate Furfural, ethyl levulinate, and acetic anhydride are reacted to form the starting compound ethyl 6-(5-acetylfuran-2-yl)-4-oxohexanoate, according to a method described in the Gordon applications, the entire disclosure of which are incorporated herein by reference.

For the hydrogenation reaction, 300 g of ethyl 6-(5-acetylfuran-2-yl)-4-oxohexanoate and 3.0 g of 64 weight percent Ni on Silica catalyst are added to a 600 mL stirred Parr reactor. Alternative catalysts such as Rh, Re, Ru, Pd, Pt, Ir, Cu, Cr, or Fe on supports such as carbon, silica, or alumina can also be used. The reactive conditions will be selected to produce a reduced mixture for example where the furan ring is substantially hydrogenated. The reactor is purged of air using vacuum and nitrogen cycles and then is charged with hydrogen gas to an initial pressure of 200 psig. The system is run at 200 psig of hydrogen gas with temperatures of 75° C. for 4 hours, then 100° C. for 2 hours, and then 125° C. for 100 hours. The resulting reduced mixture includes but is not limited to ethyl 6-(5-acetyltetrahydrofuran-2-yl)-4-oxohexanoate, ethyl 6-(5-acetyltetrahydrofuran-2-yl)-4-hydroxyhexanoate, or 5-(2-(5-acetyltetrahydrofuran-2-yl)ethyl) dihydrofuran-2(3H)-one.

For the hydrodeoxygenation reaction, an appropriate catalyst such as Ni on SiAl, Pt on SiAl, or other precious metals such as Rh, Re, Ru, Pd, Pt, Ir, Cu, Cr, or Fe on an acidic support, is prepared and activated as described in previous Examples. The hydrogenation products are dissolved at 50 weight percent in methanol. The solution is pumped at 0.03 mL/min over 1 g of catalyst (LHSV≈0.6 hr$^{-1}$) packed in a one-quarter inch stainless steel tube at a temperature range of 220° C. to 240° C., pressure of 470 psig of hydrogen and hydrogen gas feed of 100 mL/min(GHSV≈2000 hr$^{-1}$). The effluent is collected, and methyl decanoate and ethyl dodecanoate are isolated from the spontaneously separating organic phase.

The reaction scheme for Example 11 is as follows:

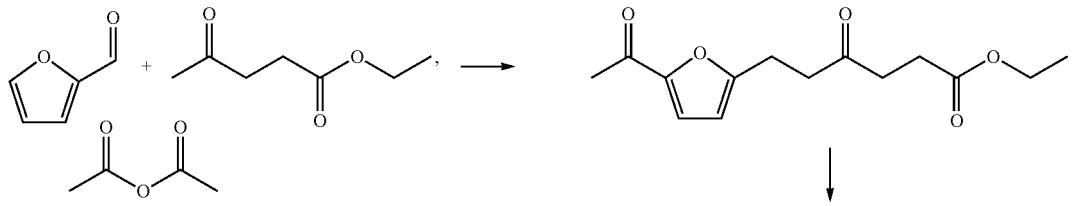

-continued

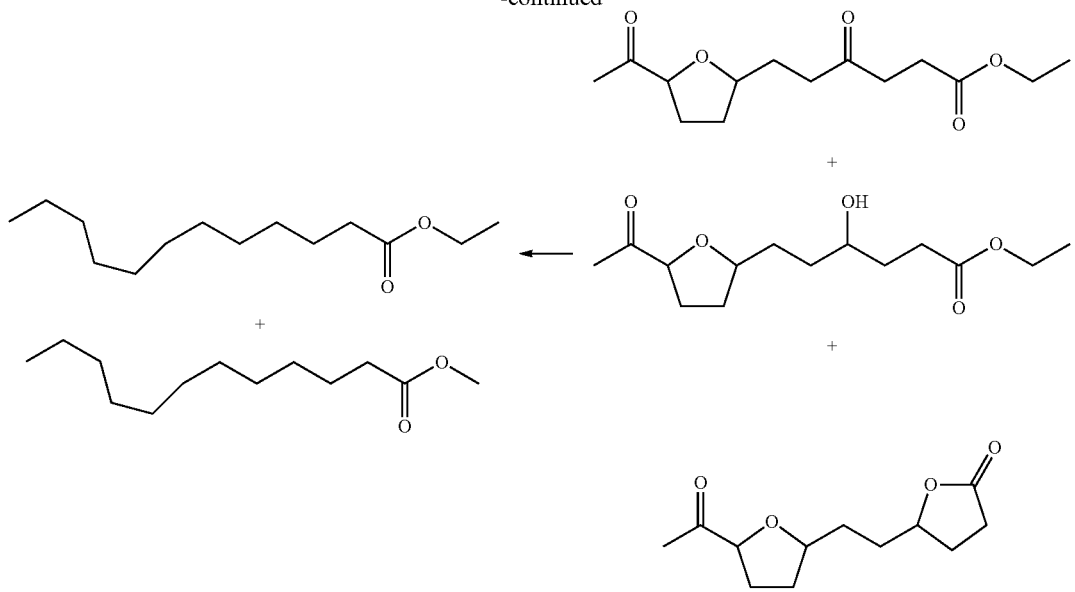

EXAMPLE 12

Method for Producing Methyl Dodecanoate and Ethyl Dodecanoate from either 4-oxo-4-(5-(3-oxobut-1-en-1-yl)furan-2-yl)butanoic acid or 4-oxo-4-(5-(3-oxobutyl)furan-2-yl)butanoic acid Furfural, acetone, and succinic anhydride are reacted to form the starting compounds of either 4-oxo-4-(5-(3-oxobut-1-en-1-yl)furan-2-yl)butanoic acid or 4-oxo-4-(5-(3-oxobutyl)furan-2-yl)butanoic acid, according to a method described in U.S. Provisional Application No. 61/669,775, filed Jul. 10, 2012, entitled "Compounds and Methods for the Production of Long Chain Hydrocarbons From Biological Sources," the entire disclosure of which is incorporated herein by reference. These species are then esterified with ethanol in the usual way to form ethyl 4-oxo-4-(5-(3-oxobut-1-en-1-yl)furan-2-yl)butanoate and ethyl 4-oxo-4-(5-(3-oxobutyl)furan-2-yl)butanoate.

For the hydrogenation reaction, 300 g of either ethyl 4-oxo-4-(5-(3-oxobut-1-en-1-yl)furan-2-yl)butanoate or ethyl 4-oxo-4-(5-(3-oxobutyl)furan-2-yl)butanoate and 3.0 g of 64 weight percent Ni on Silica catalyst are added to a 600 mL stirred Parr reactor. A solvent such as ethanol is also optionally added. Alternative catalysts such as Rh, Re, Ru, Pd, Pt, Ir, Cu, Cr, or Fe on supports such as carbon, silica, or alumina can also be used. The reactive conditions will be selected to produce a reduced mixture for example where the furan ring is substantially hydrogenated. The reactor is purged of air using vacuum and nitrogen cycles and then is charged with hydrogen gas to an initial pressure of 200 psig. The system is run at 200 psig of hydrogen gas with temperatures of 75° C. for 4 hours, then 100° C. for 2 hours, and then 125° C. for 100 hours. The resulting reduced mixture includes but is not limited to ethyl 4-oxo-4-(5-(3-oxobutyl)tetrahydrofuran-2-yl)butanoate, ethyl 4-(5-(3-hydroxybutyl)tetrahydrofuran-2-yl)-4-oxobutanoate and 5'-(3-oxobutyl)hexahydro-[2,2'-bifuran]-5(2H)-one.

For the hydrodeoxygenation reaction, an appropriate catalyst such as Ni on SiAl, Pt on SiAl, or other precious metals such as Rh, Re, Ru, Pd, Pt, Ir, Cu, Cr, or Fe on an acidic support, is prepared and activated as described in previous Examples. The reduced mixture is dissolved at 50 weight percent in methanol. The solution is pumped at 0.03 mL/min over 1 g of catalyst (LHSV≈0.6 hr$^{-1}$) packed in a one-quarter inch stainless steel tube at a temperature range of 220° C. to 240° C., pressure of 470 psig of hydrogen and hydrogen gas feed of 100 mL/min(GHSV≈2000 hr$^{-1}$). The effluent is collected and methyl dodecanoate and ethyl dodecanoate are isolated from the spontaneously separating organic phase.

The reaction scheme for Example 12 is as follows:

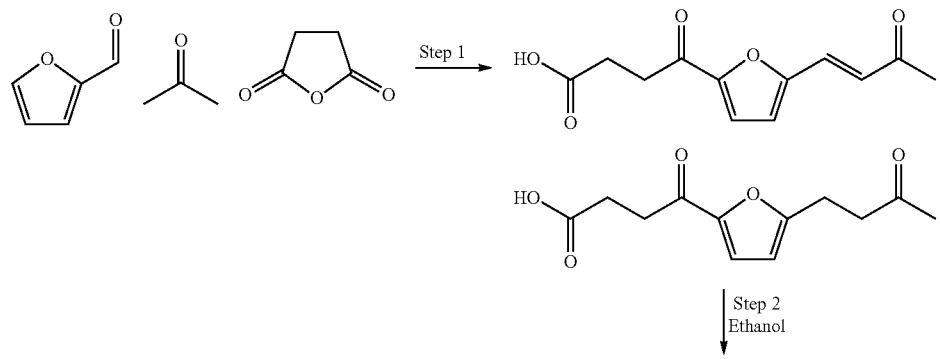

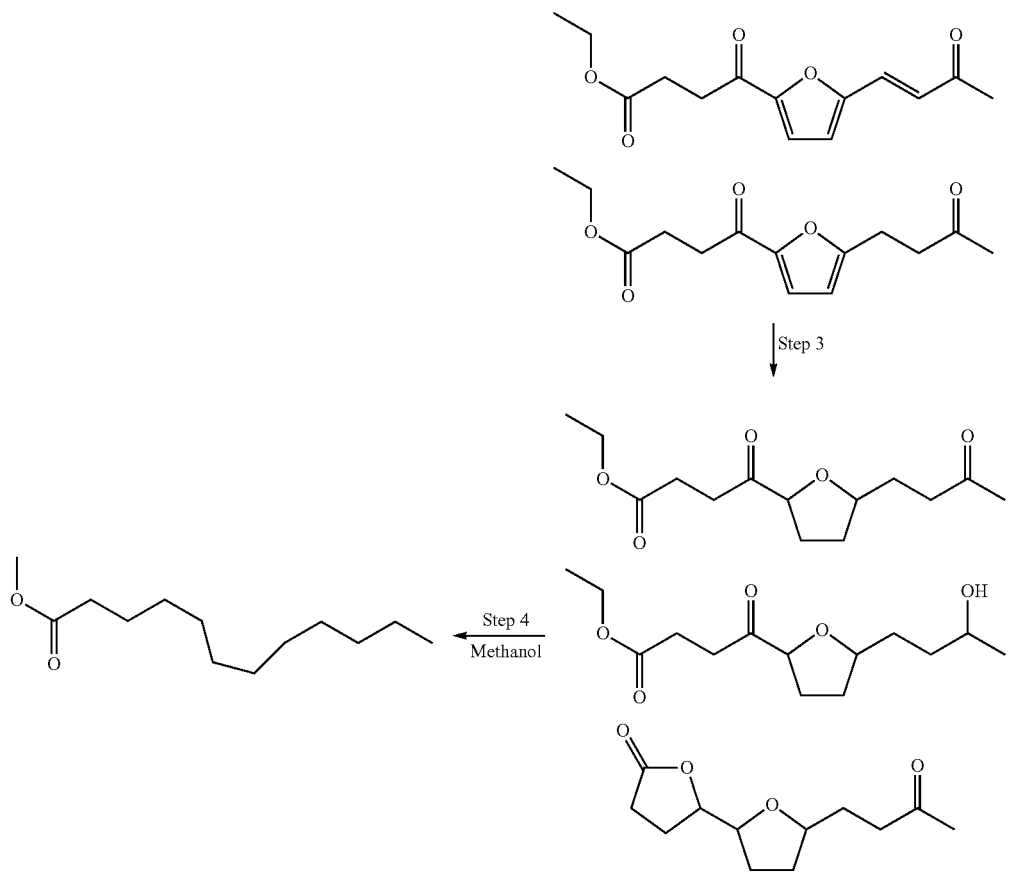

EXAMPLE 13

Method for Producing a Di-Ester or Di-Acid Compounds

Furfural, ethyl levulinate, and succinic anhydride are reacted to form the starting compounds of either 4-(5-(6-ethoxy-3,6-dioxohex-1-en-1-yl)furan-2-yl)-4-oxobutanoic acid or 4-(5-(6-ethoxy-3,6-dioxohexyl)furan-2-yl)-4-oxobutanoic acid, according to a method described in U.S. Provisional Application No. 61/669,775, filed Jul. 10, 2012, entitled "Compounds and Methods for the Production of Long Chain Hydrocarbons From Biological Sources.", the entire disclosure of which is incorporated herein by reference. These species are then esterified with ethanol in the usual way to form di-ester compounds, ethyl 6-(5-(4-ethoxy-4-oxobutanoyl)furan-2-yl)-4-oxohex-5-enoate, and ethyl 6-(5-(4-ethoxy-4-oxobutanoyl)furan-2-yl)-4-oxohexanoate.

For the hydrogenation reaction, 300 g of either ethyl 6-(5-(4-ethoxy-4-oxobutanoyl)furan-2-yl)-4-oxohex-5-enoate, or ethyl 6-(5-(4-ethoxy-4-oxobutanoyl)furan-2-yl)-4-oxohexanoate and 3.0 g of 64 weight percent Ni on Silica catalyst are added to a 600 mL stirred Parr reactor. A solvent such as ethanol is also optionally added. Alternative catalysts such as Rh, Re, Ru, Pd, Pt, Ir, Cu, Cr, or Fe on supports such as carbon, silica, or alumina can also be used. The reactive conditions will be selected to produce a reduced mixture for example where the furan ring is substantially hydrogenated. The reactor is purged of air using vacuum and nitrogen cycles and then is charged with hydrogen gas to an initial pressure of 200 psig. The system is run at 200 psig of hydrogen gas with temperatures of 75° C. for 4 hours, then 100° C. for 2 hours, and then 125° C. for 100 hours. The resulting reduced mixture includes but is not limited to ethyl 64544-ethoxy-4-oxobutanoyl)tetrahydrofuran-2-yl)-4-oxohexanoate, ethyl 6-(5-(4-ethoxy-4-oxobutanoyl)tetrahydrofuran-2-yl)-4-hydroxyhexanoate and 5'-(2-(5-oxotetrahydrofuran-2-yl)ethyl)hexahydro-[2,2'-bifuran]-5(2H)-one.

For the hydrodeoxygenation reaction, an appropriate catalyst such as Ni on SiAl, Pt on SiAl, or other precious metals such as Rh, Re, Ru, Pd, Pt, Ir, Cu, Cr, or Fe on an acidic support, is prepared and activated as described in previous Examples. The reduced mixture dissolved at 50 weight percent in methanol. The solution is pumped at 0.03 mL/min over 1 g of catalyst (LHSV≈0.6 hr$^{-1}$) packed in a one-quarter inch diameter stainless steel tube at a temperature range of 220° C. to 240° C., pressure of 470 psig of hydrogen and hydrogen gas feed of 100 mL/min(GHSV≈2000 hr$^{-1}$). The effluent is collected, and dimethyl tetradecanedioate, diethyl tetradecanedioate and methyl ethyl tetradecanedioate are isolated from the spontaneously separating organic phase.

The reaction scheme for Example 13 is as follows:

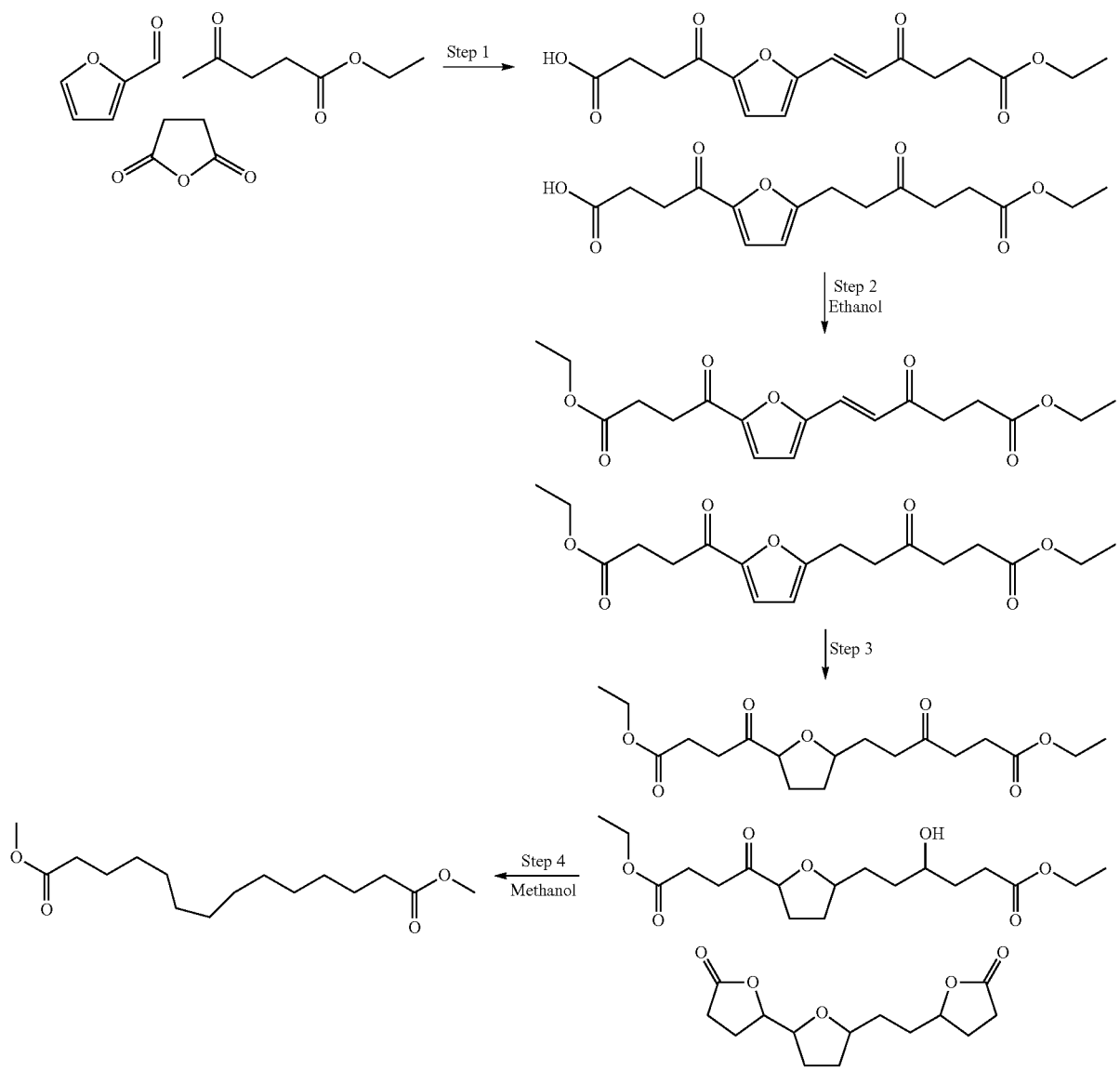

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40° C." is intended to mean "about 40° C."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

What is claimed is:

1. A method of reacting an oxygenated hydrocarbon to form a saturated alkyl acid or ester where the oxygenated hydrocarbon contains:

i. At least one furan group,
ii. At least one oxygen-containing group selected from the group consisting of acid groups, ester groups, and combinations of acid and ester groups, and
iii. At least one carbonyl-containing group selected from the group consisting of aldehyde groups, ketone groups, and combinations of aldehyde and ketone groups, wherein the method comprises:
(a) hydrogenating the oxygenated hydrocarbon in the presence of a first catalyst to reduce the number of multiple bonds and produce a reduced mixture having multiple components wherein each component of the reduced mixture contains at least one acid, ester or lactone group; and,
(b) hydrodeoxygenating the reduced mixture in the presence of a second catalyst to form a saturated alkyl acid or ester.

2. The method of claim 1 where the oxygenated hydrocarbon further contains at least one alkene.

3. The method of claim 1, wherein the first catalyst comprises a metal selected from the group consisting of nickel, ruthenium, palladium, rhenium, platinum, rhodium, iridium, copper, chromium, iron, cobalt, and combinations thereof.

4. The method of claim 1, wherein the first catalyst comprises nickel.

5. The method of claim 1 wherein the first catalyst comprises ruthenium.

6. The method of claim 1, wherein the first catalyst comprises platinum.

7. The method of claim 1, wherein the hydrodeoxygenation is performed at a temperature of about 220° C. to about 270° C.

8. The method of claim 1, wherein the hydrodeoxygenation is performed at a pressure of about 3 MPa of hydrogen.

9. The method of claim 1, wherein the hydrodeoxygenation is a performed as a neat reaction.

10. The method of claim 1, wherein the reduced mixture is dissolved in an aqueous solution during hydrodeoxygenation.

11. The method of claim 1, wherein the reduced mixture is dissolved in a solution containing water and an alcohol during hydrodeoxygenation.

12. The method of claim 11, wherein the aqueous solution comprises about 60% water, based on the total weight of the solution, and about 40% ethanol, based on the total weight of the solution.

13. The method of claim 1, wherein the reduced mixture is dissolved in methanol during hydrodeoxygenation to form a reduced mixture/methanol solution.

14. The method of claim 13, wherein the reduced mixture comprises about 50 weight percent of the reduced mixture/methanol solution.

15. The method of claim 1 wherein the second catalyst comprises a metal selected from the group consisting of nickel, ruthenium, palladium, rhenium, platinum, rhodium, iridium, copper, chromium, iron, cobalt, and combinations thereof on an acidic support.

16. The method of claim 1 wherein the second catalyst comprises platinum on a silica alumina support.

17. The method of claim 1, wherein the second catalyst comprises nickel on a silica alumina support.

18. The method of claim 1 wherein:
(a) the oxygenated hydrocarbon has the structure of Formula I; and,

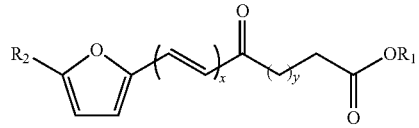

Formula I (b) the resulting saturated alkyl ester or acid has the structure of Formula II

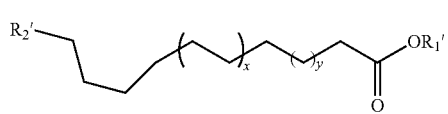

Formula II wherein:
$R_1$ and $R_1'$ are each individually selected from the group consisting of hydrogen and alkyl,
$R_2$ is selected from the group consisting of hydrogen, alkyl, hydroxyalkyl, and oxo-alkyl,
$R_2'$ is the same as $R_2$, with the proviso that when $R_2$ is hydroxyalkyl or oxo-alkyl, $R_2'$ is the alkyl resulting from the hydrodeoxygenation of $R_2$, x is 1 to 3, and
y is 1 to 2.

19. The method of claim 1 wherein:
(a) the oxygenated hydrocarbon has the structure of Formula III; and,

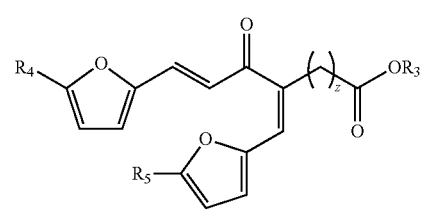

Formula III (b) resulting saturated alkyl ester or acid has the branched structure of Formula IV

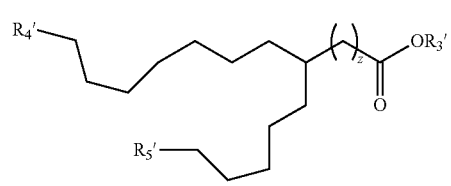

Formula IV wherein:
$R_3$ and $R_3'$ are each individually selected from the group consisting of hydrogen and alkyl,
$R_4$ and $R_5$ are each independently selected from the group consisting of hydrogen, alkyl, and hydroxyalkyl,
$R_4'$ is the same as $R_4$, with the proviso that when $R_4$ is hydroxyalkyl, $R_4'$ is the alkyl resulting from the hydrodeoxygenation of $R_4$,
$R_5'$ is the same as $R_5$, with the proviso that when $R_5$ is hydroxyalkyl, $R_5'$ is the alkyl resulting from the hydrodeoxygenation of $R_5$, and
z is 1 to 2.

20. The method of claim 1 wherein:
(a) the oxygenated hydrocarbon has the structure of Formula V; and,

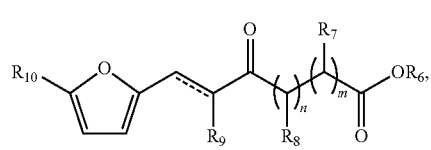

Formula V (b) the resulting saturated branched alkyl ester or acid has the structure of Formula VI:

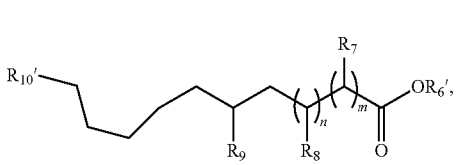

Formula VI wherein:
the dashed line denotes an optional double bond,
$R_6$, $R_6'$, $R_7$, $R_8$, and $R_9$ are each independently selected from the group consisting of hydrogen and alkyl, $R_{10}$ is selected from the group consisting of hydrogen, alkyl, and substituted alkyl, $R_{10}'$ is the same as $R_{10}$, with the proviso that when $R_{10}$ is substituted alkyl, $R_{10}'$ is the alkyl group resulting from the hydrodeoxygenation of $R_{10}$, m is 1 to 4, and n is 1 to 4.

\* \* \* \* \*